US011197962B2

(12) United States Patent
Reich

(10) Patent No.: US 11,197,962 B2
(45) Date of Patent: Dec. 14, 2021

(54) WAVEFORM RECONSTRUCTION FOR ULTRASOUND TIME OF FLIGHT MEASUREMENTS

(71) Applicant: Verily Life Sciences LLC, South San Francisco, CA (US)

(72) Inventor: Adam Reich, Oakland, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 34 days.

(21) Appl. No.: 16/267,154

(22) Filed: Feb. 4, 2019

(65) Prior Publication Data

US 2019/0262543 A1   Aug. 29, 2019

Related U.S. Application Data

(60) Provisional application No. 62/635,440, filed on Feb. 26, 2018.

(51) Int. Cl.
*A61M 5/315* (2006.01)
*G01F 1/66* (2006.01)
(Continued)

(52) U.S. Cl.
CPC .... *A61M 5/31525* (2013.01); *A61M 5/14244* (2013.01); *A61M 5/1723* (2013.01);
(Continued)

(58) Field of Classification Search
CPC .............. A61M 5/315; A61M 5/31511; A61M 5/31525; A61M 5/31535; A61M 5/31546;
(Continued)

(56) References Cited

U.S. PATENT DOCUMENTS 4,358,839 A    11/1982 Wittke
4,936,143 A *   6/1990 Schutten ................ G01D 5/243
                                          73/597
(Continued)

FOREIGN PATENT DOCUMENTS

CN       101925374 A    12/2012
CN       206505275 U     9/2017
(Continued)

OTHER PUBLICATIONS

Results of STIC Search, conducted by EIC 3700 on Jul. 21, 2021. (Year: 2021).*
(Continued)

*Primary Examiner* — Kami A Bosworth
(74) *Attorney, Agent, or Firm* — Christensen O'Connor Johnson Kindness PLLC

(57) ABSTRACT

A plunger head to measure fluid in a drug cartridge includes a transducer coupled to emit ultrasonic signals, and a power source. A controller is coupled to the transducer and the power source, and the controller includes logic that when executed by the controller causes the plunger head to perform operations. For example the plunger head may emit the ultrasonic signals along a length of the drug cartridge, when the plunger head is disposed in the drug cartridge, and receive the ultrasonic signals after the ultrasonic signals are reflected from a dispensing end of the drug cartridge. The plunger head may then determine when the ultrasonic signals received by the transducer have an absolute value of amplitude greater than a first threshold value, and associate a timestamp with the ultrasonic signals received that have the absolute value of amplitude greater than the first threshold value.

9 Claims, 5 Drawing Sheets

(51) Int. Cl.
*A61M 5/172* (2006.01)
*A61M 5/142* (2006.01)
*A61M 5/31* (2006.01)

(52) U.S. Cl.
CPC .... *A61M 5/31546* (2013.01); *A61M 5/31568* (2013.01); *G01F 1/663* (2013.01); *A61M 2005/3126* (2013.01); *A61M 2205/3375* (2013.01); *A61M 2205/502* (2013.01); *A61M 2205/8206* (2013.01); *A61M 2230/201* (2013.01)

(58) Field of Classification Search
CPC .......... A61M 5/31568; A61M 5/31573; A61M 2005/3126; A61M 2205/3327; A61M 2205/3375; A61M 2205/3379; A61M 2205/52; G01F 1/663; G01F 23/296; G01F 23/2962; G01S 7/521; G01S 15/02; G01S 15/08; G01S 15/50; G01S 15/06; G01S 15/10–36; G01S 15/58–586
See application file for complete search history.

(56) References Cited

U.S. PATENT DOCUMENTS

| | | | |
|---|---|---|---|
| 5,311,871 A | 5/1994 | Yock | |
| 5,319,972 A * | 6/1994 | Oblak | G01S 7/527 73/290 R |
| 5,678,189 A | 10/1997 | Barnes | |
| 5,728,074 A | 3/1998 | Castellano et al. | |
| 5,826,066 A | 10/1998 | Jardine et al. | |
| 6,151,014 A * | 11/2000 | Zloter | G01S 7/52004 178/18.01 |
| 6,267,042 B1 * | 7/2001 | Nagai | F15B 19/00 92/5 R |
| 6,585,698 B1 | 7/2003 | Packman et al. | |
| 6,816,436 B1 * | 11/2004 | Bachert | G01S 7/527 367/908 |
| 6,871,148 B2 | 3/2005 | Morgen et al. | |
| 7,927,281 B2 | 4/2011 | Wheeler | |
| 8,226,599 B2 | 7/2012 | Engle | |
| 8,556,866 B2 | 10/2013 | Krulevitch et al. | |
| 8,560,271 B2 | 10/2013 | Koehler et al. | |
| 8,817,258 B2 | 8/2014 | Whalley et al. | |
| 9,008,764 B2 | 4/2015 | Larsen | |
| 9,101,723 B2 | 8/2015 | Larsen | |
| 9,250,111 B2 | 2/2016 | Whalley et al. | |
| 9,255,830 B2 | 2/2016 | Whalley et al. | |
| 10,365,247 B2 * | 7/2019 | Paradise | G01S 11/14 |
| 10,391,255 B2 | 8/2019 | Krasnow et al. | |
| 2004/0079615 A1 * | 4/2004 | Furneaux | G07D 1/00 194/215 |
| 2005/0209601 A1 | 9/2005 | Bowman et al. | |
| 2008/0188813 A1 | 8/2008 | Miller et al. | |
| 2008/0243088 A1 | 10/2008 | Evans | |
| 2009/0043253 A1 | 2/2009 | Podaima | |
| 2009/0069742 A1 | 3/2009 | Larsen | |
| 2010/0288036 A1 * | 11/2010 | Volkwein | G01S 15/02 73/114.29 |
| 2011/0009824 A1 | 1/2011 | Yodfat et al. | |
| 2011/0313395 A1 | 12/2011 | Krulevitch et al. | |
| 2012/0101451 A1 | 4/2012 | Boit et al. | |
| 2012/0302849 A1 | 11/2012 | Grant et al. | |
| 2013/0116666 A1 | 5/2013 | Shih et al. | |
| 2013/0283917 A1 * | 10/2013 | Coonrod | E21B 33/061 73/597 |
| 2013/0310756 A1 | 11/2013 | Whalley et al. | |
| 2014/0249410 A1 | 9/2014 | Uber et al. | |
| 2014/0379874 A1 | 12/2014 | Starr et al. | |
| 2015/0085613 A1 * | 3/2015 | Petersen | G01D 5/48 367/99 |
| 2015/0112316 A1 | 4/2015 | Cudak et al. | |
| 2015/0174330 A1 * | 6/2015 | Nagel | G01F 17/00 604/218 |
| 2015/0174342 A1 | 6/2015 | Mitrosky et al. | |
| 2015/0209510 A1 | 7/2015 | Burkholz et al. | |
| 2016/0022539 A1 | 1/2016 | Daines | |
| 2016/0030683 A1 | 2/2016 | Taylor et al. | |
| 2016/0074587 A1 | 3/2016 | Searle et al. | |
| 2016/0274067 A1 | 9/2016 | Walker et al. | |
| 2017/0136185 A1 * | 5/2017 | Rios | A61M 5/31511 |
| 2017/0224288 A1 | 8/2017 | Halter et al. | |
| 2017/0351836 A1 | 12/2017 | Thornton et al. | |
| 2018/0200451 A1 * | 7/2018 | Shekalim | G01F 11/029 |
| 2019/0054252 A1 * | 2/2019 | Amschler | A61M 5/31571 |
| 2020/0230325 A1 * | 7/2020 | Bengtsson | A61M 5/31568 |

FOREIGN PATENT DOCUMENTS

| | | |
|---|---|---|
| WO | 2009092807 A | 7/2009 |
| WO | 2014/009442 A1 | 1/2014 |
| WO | 2017155672 A1 | 9/2017 |

OTHER PUBLICATIONS

Li et al., "An improved automatic time-of-flight picker for medical ultrasound tomography," Ultrasonics, vol. 49, 2009, pp. 61-72.
International Search Report and Written Opinion dated May 14, 2018 from the International Searching Authority for International Application No. PCT/US2018/019917, filed Feb. 27, 2018, 30 pages.
International Search Report and Written Opinion from the International Searching Authority dated Jun. 8, 2017 for International Application No. PCT/US2017/017821, filed Feb. 14, 2017, 16 pages.
U.S. Appl. No. 15/887,700, Drug Cartridge With Acoustic Reflector, filed Feb. 2, 2018, 26 pages.
Chinese Office Action, dated Jan. 23, 2021, in corresponding Chinese Patent Application No. 201910141065.0, 10 pages.
Chinese Office Action, dated Jan. 6, 2021, in corresponding Chinese Patent Application No. 201910141065.0, 10 pages.

* cited by examiner

WAVEFORM RECONSTRUCTION FOR ULTRASOUND TIME OF FLIGHT MEASUREMENTS

CROSS-REFERENCE TO RELATED APPLICATIONS

This application claims the benefit of U.S. Provisional Application No. 62/635,440, filed Feb. 26, 2018, which is hereby incorporated by reference in its entirety.

TECHNICAL FIELD

This disclosure relates generally to dispensing fluid and in particular but not exclusively, relates to tracking injection quantities.

BACKGROUND INFORMATION

Measuring the quantity and recording the timing of a drug's administration is an integral part of many disease treatments. For many treatments, to achieve the best therapeutic effect, specific quantities of a drug may need to be injected at specific times of day. For example, individuals suffering from diabetes may be required to inject themselves regularly throughout the day in response to measurements of their blood glucose. The frequency and volume of insulin injections must be carefully tracked and controlled to keep the patient's blood glucose level within a healthy range.

Currently, there are a limited number of methods or devices capable of tracking drug administration without requiring the user to manually measure and record the volume, date, and time. A variety of glucose injection syringes/pens have been developed, but there is much room for significant advancement in the technology in order to reduce the size, lower the cost, enhance the functionality, and improve the accuracy. Thus, the current technology may not be an ideal long-term solution. For example, current insulin pens are often disposable, but do not include dosage tracking. A smaller portion of the market is composed of reusable pens which are more expensive, and still do not include accurate dosage-tracking capabilities.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus, system, and method for waveform reconstruction for ultrasound time of flight measurements are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Drug cartridges may be used in insulin pens to dispense insulin into a user. When the user needs to inject insulin, the user may put a drug cartridge in an insulin pen and inject themselves with a desired dose of insulin. However, with conventional pens/cartridges it is difficult to track the dose injected over time, since the user would manually have to record time, dosage amount, etc. Here, an apparatus, system, and method for automated dosage tracking using ultrasound time of flight is disclosed.

Figure 1A:
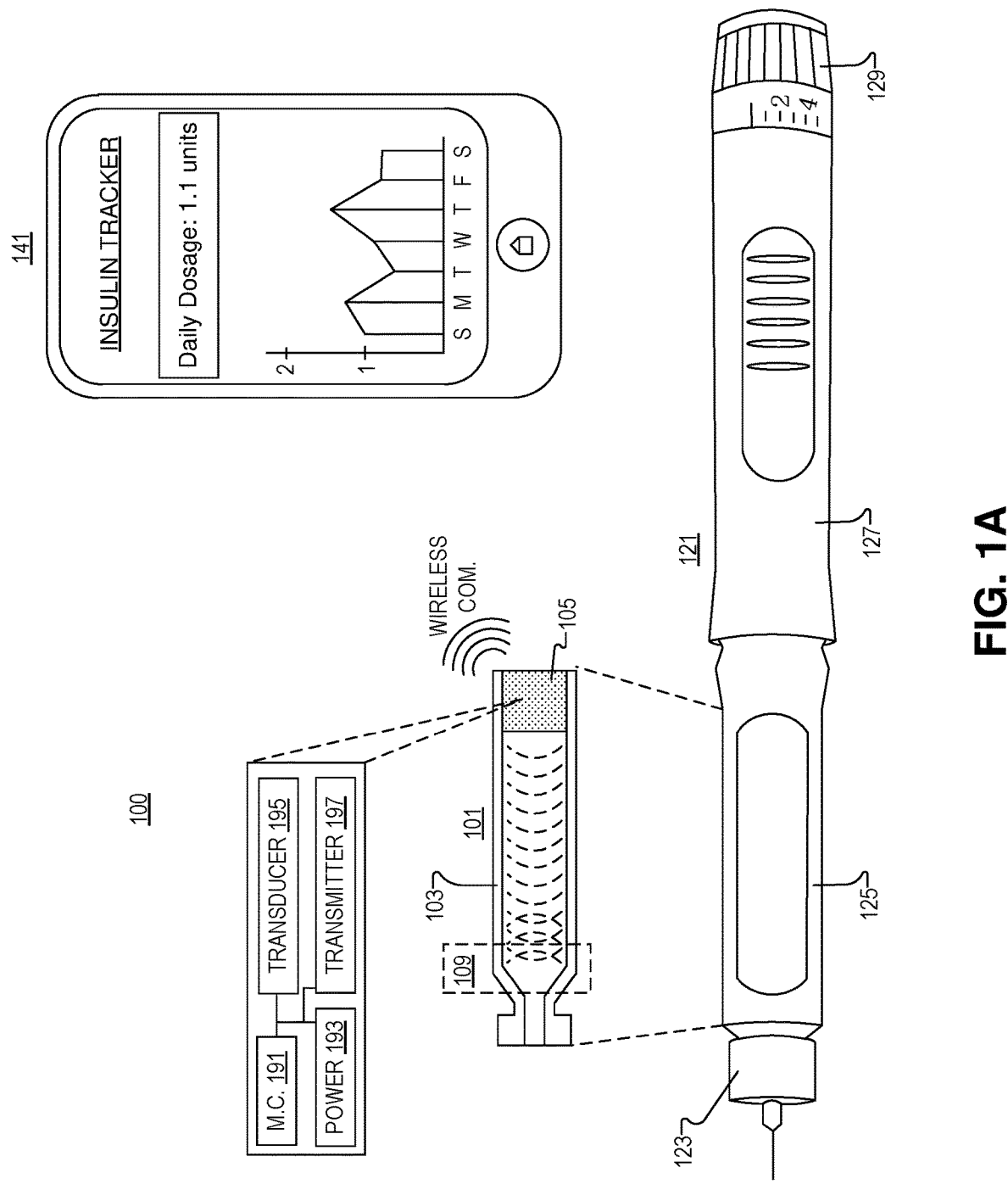
FIG. 1A illustrates a system for fluid injection and dosage tracking, in accordance with an embodiment of the disclosure.

Ultrasound transducers may be used for range finding applications in enclosed environments (e.g., the injection pen cartridge depicted in FIG. 1A). The accuracy requirements for these close-range measurements are commonly on the order of millimeters. Operating within a closed tube, the ultrasonic energy which emanates from the transducer travels not only along the axis of the tube, but some amount also bounces along the side walls, creating patterns of standing waves which lead to fluctuation in the return waveform shape and intensity.

While the variation in waveform shape still permits acceptable time of flight measurement accuracy, when used in drug delivery devices, measurement accuracy may need to be on the order of 100 microns to ensure accurate dosage measurement data. This high resolution requirement poses increased demands on system performance. The fluctuations in return signal shape and intensity greatly complicate the accurate measurement of the waveform time of flight, requiring use of a matched filter or similar approaches.

One obstacle to implementing such an algorithm is the need for very high frequency sampling of an analog waveform (e.g., sampling on the order of 10 MHz). In the case of a disposable device, such as a drug cartridge, the required cost and power consumption of such an analog to digital converter may be prohibitive.

The disclosure presented herein makes use of a microprocessor's (one embodiment of a "controller") digital inputs (either general-purpose input/output or hardware interrupts) to obtain timestamps for each time the waveform generated by the ultrasound crosses a given threshold with either a rising or falling edge. This process may be repeated for two or more unique threshold values (nominally one above the neutral axis of the waveform, and one below), yielding a set of points known to lie on the waveform at two or more Y values.

These points can then be fit using a spline or similar function (e.g., cubic spline or other polynomial interpolation), to generate a waveform sharing the key features of the original signal.

In instances where the frequency of threshold crossings is low, the cubic spline fit may not be ideal, resulting in high amplitude, low frequency behavior (see e.g., FIG. 2A "cubic spline reconstruction line" between 0.000066 and 0.000068 second time intervals) that does not reflect the original waveform. This may be easily eliminated through use of a digital high-pass filter. The approaches presented herein leverage the relatively low cost of high speed digital I/O on microprocessors to obtain the basic structure of a high frequency analog signal. In some embodiments, an envelope filter may be used on the return waveform to generate the signal envelope, and rising and falling edges of the waveform may be repeatedly measured across varying thresholds. Further, other approaches to a cubic spline may be used, such as simple interpolation between measured points.

It is appreciated that the reconstructed waveform (or "curve") is compared to a template or expected waveform recorded at a known position of the plunger head in the cartridge. The difference in position between these two waveforms may be used to evaluate of the relative motion of the stopper. While using a single reconstructed waveform to compute time of flight may be possible, the resultant measurement would be subject to the same accuracy limitations/errors as just using the first threshold crossing. Looking at multiple shifts in the wave form allows for accurate measurement of the progression of the plunger head.

The techniques disclosed herein are advantageous because they reduce the processing load placed on the controller in the plunger head. This facilitates both reduced battery consumption (extending the working lifetime of the plunger head) and also reduces the hardware requirements of the controller (reducing the overall cost and size of the device).

The following description will discuss the embodiments mentioned above, and other embodiments, as they relate to the figures.

FIG. 1A illustrates a system 100 for fluid injection and dosage tracking, in accordance with an embodiment of the disclosure. System 100 includes drug cartridge 101, injection pen 121, and processing device 141.

Drug cartridge 101 includes cartridge body 103, plunger head 105, and dispensing end 109. One of ordinary skill in the art will appreciate that drug cartridge 101 may take other forms, may be disposed in a pump (e.g., insulin pump), and may even be the body of a syringe, in accordance with the teachings of the present disclosure.

In the depicted embodiment, plunger head 105 is adapted to fit within the interior cavity of drug cartridge body 103, and plunger head 105 includes transducer 195, microcontroller 191, power supply 193, and transmitter 197. Microcontroller 191 is coupled to transducer 195, such that in response to a control signal from microcontroller 191, transducer 195 emits ultrasonic waves into the interior cavity of drug cartridge 101. Power supply 193 is coupled to microcontroller 191 to power microcontroller 191. Wireless (or, in other embodiments, wired) transmitter 197 may be coupled to microcontroller 191, such that in response to ultrasonic waves being reflected back to plunger head 105 from dispensing end 109, microcontroller 191 calculates an amount of liquid in drug cartridge 101 and wireless transmitter 197 transmits data (including information about the amount of liquid in drug cartridge 101) to processing device 141.

Injection pen 121 is a hand-held device and includes needle 123, chamber 125 (shaped to receive drug cartridge 101), body 127 (including a drug dispensing actuator to push in plunger head 105 and extract fluid from drug cartridge 101), and a drug delivery control switch 129 (twist the switch to control the dosage). However, as one of ordinary skill in the art will appreciate, injection pen 121 can take other configurations and have other components. It is appreciated that injection pen 121 may be a generic store-bought pen, and drug cartridge 101 is configured to fit in most generic pens.

Processing device 141 (e.g., a smartphone, tablet, general purpose computer, distributed system, servers connect to the internet, or the like) may be coupled to receive data from drug cartridge 101 to store/analyze this data. For instance, in the depicted embodiment, processing device 141 is a smartphone, and the smartphone has an application running recording how much insulin has been spent from pen 121. Moreover the application is plotting how much insulin has been dispensed by the user over the past week. This information may have been received directly from microcontroller 191/transmitter 197, or may have been acquired from pen 121 if pen 121 includes signal amplification circuitry or a direct plug-in (micro USB port or the like). One of ordinary skill in the art will appreciate that there are many ways processing device 141 can parse the injection data and electrically couple to drug cartridge 101, in accordance with the teachings of the present disclosure.

Figure 1B:
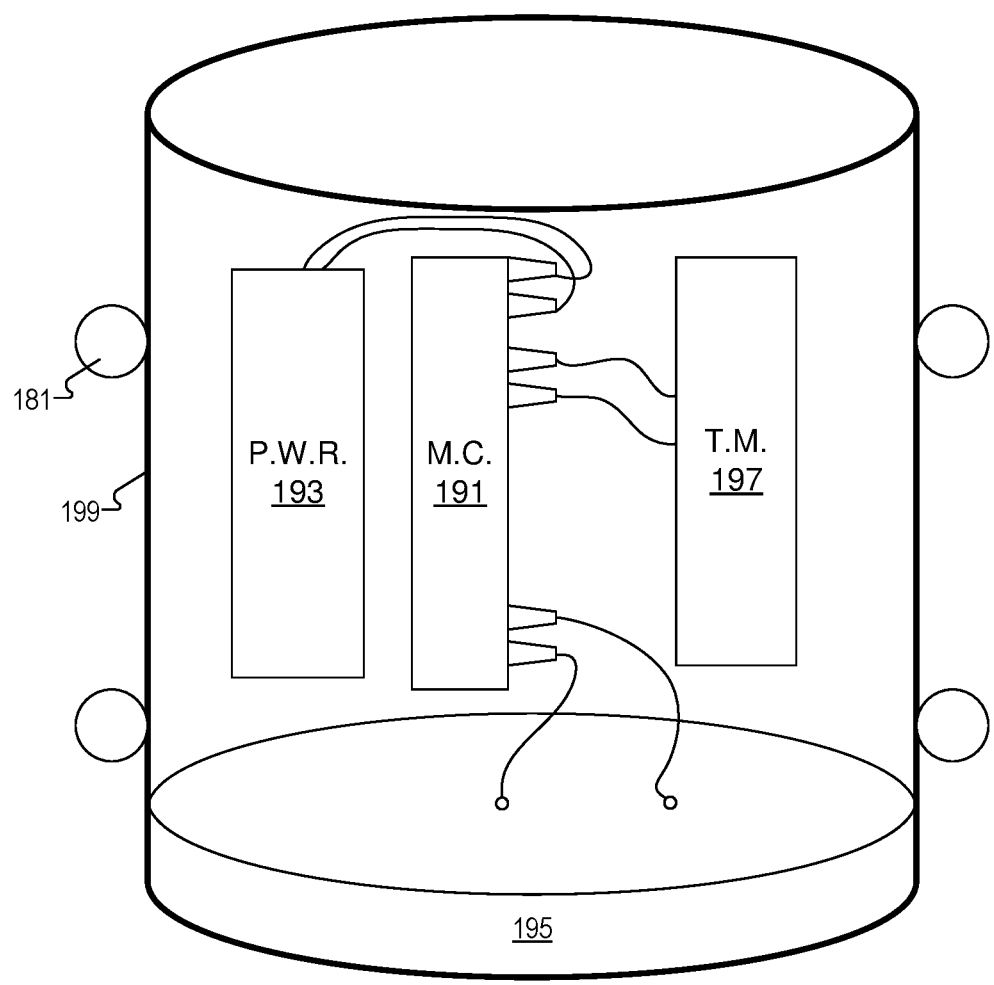
FIG. 1B illustrates the plunger head for fluid injection and dosage tracking depicted in FIG. 1A, in accordance with an embodiment of the disclosure.

FIG. 1B illustrates plunger head 105 for fluid injection and dosage tracking depicted in FIG. 1A, in accordance with an embodiment of the disclosure. Like FIG. 1A, plunger head 105 includes transducer 195 (e.g., a piezoelectric transducer, coil transducer, or the like), microcontroller 191 (which is one embodiment of a "controller"), power supply 193, and transmitter 197. As shown, transducer 195 is coupled to microcontroller 191 to emit ultrasonic signals (shown as dashed lines extending away from transducer 195) in response to electrical signals from microcontroller 191. Power may be supplied by power source 193 (e.g., battery, capacitor, or the like) which is coupled to microcontroller 191, transducer 195, and transmitter 197. It is appreciated that controller 191 may include other circuitry to apply a voltage to transducer 195. For example, controller 191 may apply a charge across a piezoelectric in transducer 195, and then a switch, disposed in or around controller 191, may short the potential applied across the piezoelectric, causing the piezoelectric to vibrate and emit the ultrasonic signals.

In the depicted embodiment, the plunger head includes a sealed enclosure 199 (e.g., a metal or plastic "can"), and transducer 191, power source 193, transmitter 197 (e.g., Bluetooth, RIFD, or the like), and controller 191 are disposed inside sealed enclosure 199. It is appreciated that sealed enclosure 199 may be designed to act as a soundboard to amplify, or at least not dampen, the ultrasonic signals). Moreover, polymer 181 (e.g., an elastomer or the like) surrounds sealed enclosure 199, at least in part, to make an air-tight seal with the body of the drug cartridge in order to keep fluid from leaking out. In the depicted embodiment, polymer 181 is shaped into O-ring-like structures. However, in other embodiments, sealed enclosure 199 may be entirely surrounded (e.g., on all sides) by the polymer 181. Thus, in some embodiments, the ultrasonic signals emitted from transducer 195 travel though both sealed enclosure 199 and polymer 181 when they are emitted and when they are received.

As illustrated, the digital pins of the controller 191 are coupled to transducer 195 (e.g., via solder or the like). As stated above, it may be advantageous to use the digital pins (instead of the analog pins) to obtain timestamps for every time the waveform crosses a given threshold with either a rising or falling edge because this can reduce the processing power required.

As illustrated, controller 191 includes logic (e.g., hardware, firmware, software, or a combination thereof, that is part of controller 191 or stored in memory) that when executed by controller 191 causes plunger head 105 to perform a variety of operations. For example, plunger head 105 may emit the ultrasonic signals along a length of the drug cartridge, when plunger head 105 is disposed in the drug cartridge. Transducer 195 may receive the ultrasonic signals after the ultrasonic signals are reflected from a dispensing end of the drug cartridge 105. It is appreciated that in some embodiments the dispensing end may include additional geometry or inserts to improve ultrasonic signal reflection. After the ultrasonic signals are reflected, controller 191 may then associating a timestamp to the ultrasonic signals, when the ultrasonic signals received by the transducer have an absolute value of amplitude greater than a first threshold value. In one embodiment, associating the timestamp occurs when the ultrasonic signals received by the transducer have an absolute value of amplitude greater than the first threshold value or a second threshold value which is different than the first threshold value. Thus, there may be more than one threshold value that triggers a timestamp. Once obtained, the timestamps may be stored in memory.

The timestamp can then be used to calculate the time of flight of the ultrasonic signals. The time of flight can be used to calculate a position of the plunger head in the drug cartridge, a volume of the fluid in the drug cartridge, or a volume of the fluid dispensed from the drug cartridge. It is appreciated that data including, or derived from, the timestamp may be transmitted to an external device (see e.g., FIG. 1A) to perform these calculations.

Figure 2A:
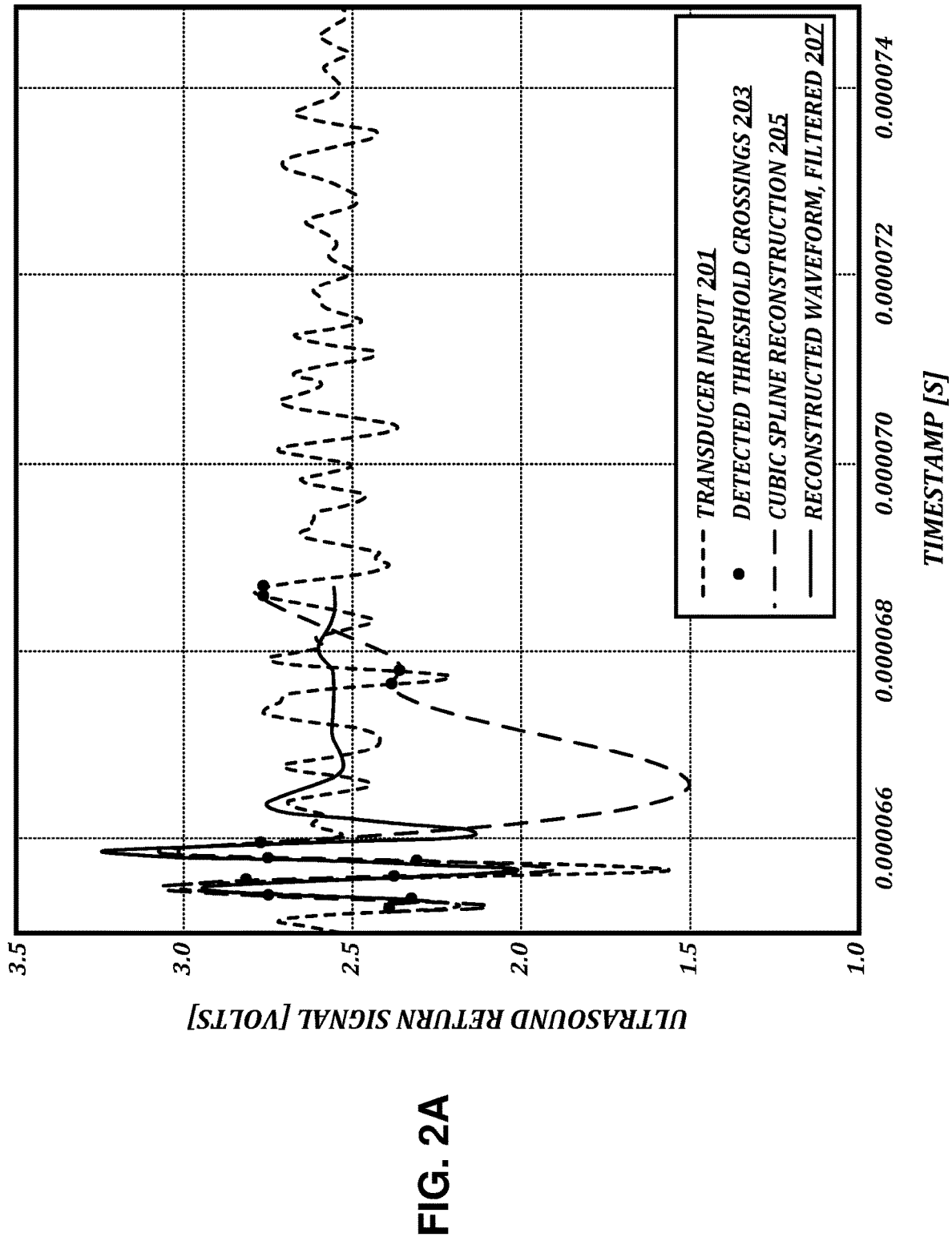
FIGS. 2A-2B illustrate experimental data showing the efficacy of the techniques for dosage tracking disclosed herein, in accordance with embodiments of the disclosure.
Figure 2B:
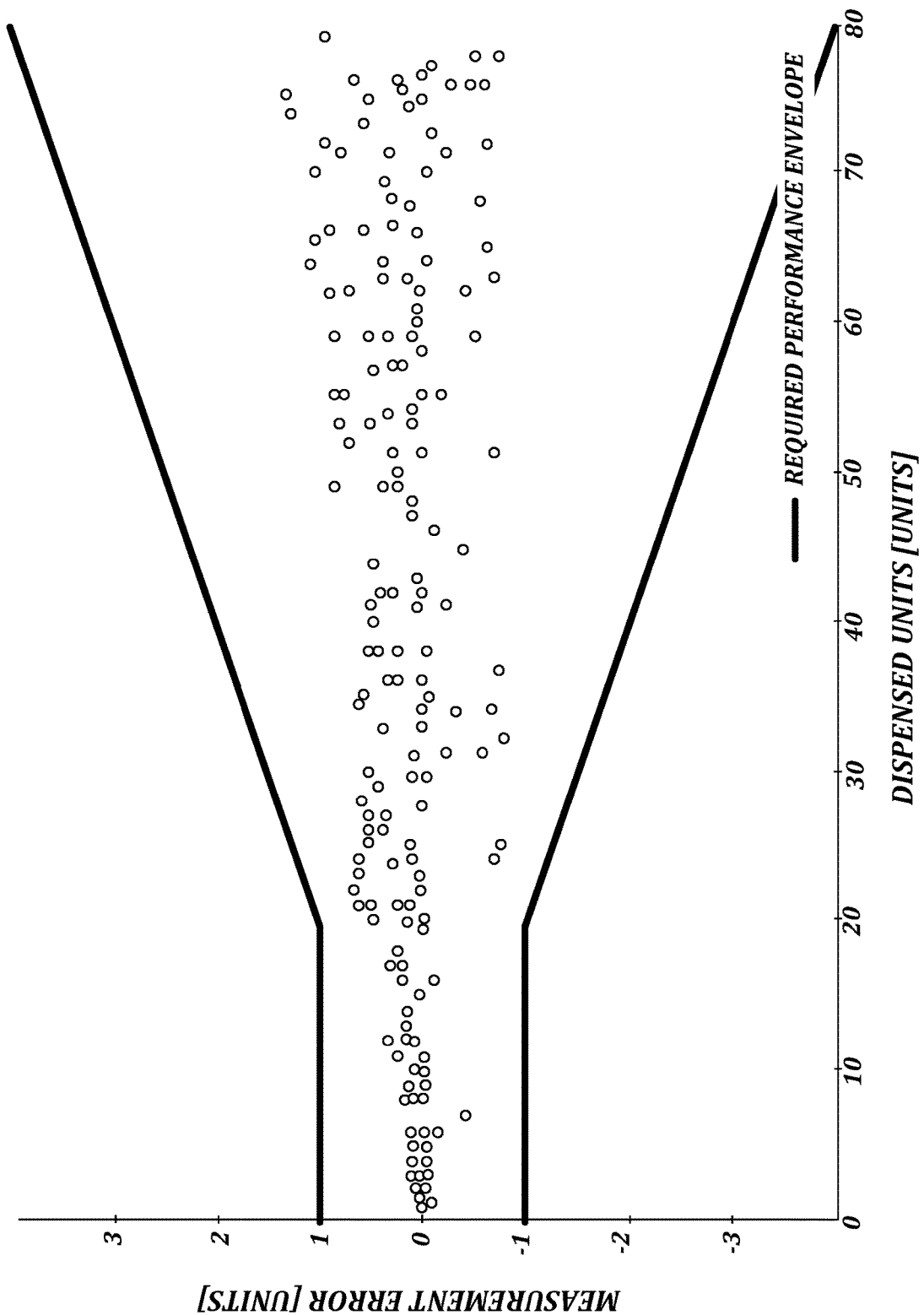

As will be shown in FIGS. 2A and 2B controller 199 may associate a plurality of timestamps, including the timestamp, with received large-amplitude ultrasonic signals and fit a curve to the plurality of timestamps. The curve may then be used to evaluate the time of flight using a matched filter or similar algorithm. In one embodiment, fitting the curve includes using a spline function or another function to yield a periodic waveform. Moreover the raw waveform calculated with the spline function may further be filtered (e.g., high-pass filter or the like) to yield a series of oscillations with substantially a same period.

FIGS. 2A-2B illustrate experimental data showing the efficacy of the techniques for dosage tracking disclosed herein, in accordance with embodiments of the disclosure.

FIG. 2A shows a graph of the actual wave signal received by the transducer (short-dashed line 201), detected threshold crossings—"timestamps" (dots 203), a cubic spline curve fitting the threshold crossings (long dashed line 205), and the filtered reconstructed waveform (solid line 207). As shown, the transducer received reflected ultrasound signals from the dispensing end of the cartridge. Accordingly, timestamps (dots 203) are recorded when the transducer voltage signal crosses predetermined threshold(s) (here ~2.4 V and ~2.7 V) on either side of the neutral Y value (here ~2.55 V) of the waveform. Thus, in the depicted embodiment, whenever the voltage across the transducer crosses (either rising or falling edge) 2.4 V or crosses 2.7 V, a timestamp is recorded. Put another way, when the ultrasonic signals received by the transducer have an absolute value of amplitude greater than a first threshold value or a second threshold value (which is different than the first threshold value) a timestamp will be recorded. By only timestamping large signals, the noise signals are removed without the need for much processing power or memory.

Once the timestamps are recorded in memory, the controller applies a fit (here a cubic spline fit). The cubic spline fit better shows when reflections are received, but the fit is not perfect (see e.g., large error between 0.000066 and 0.000068 second time intervals). Accordingly, a high-pass filter is applied to the cubic spline fit to yield a group of waves with substantially the same period. This group of waves is associated with receiving the reflection from the dispensing end of the drug cartridge, and may be used to calculate, time of flight, and associated volume measurements. One of skill in the art will appreciate that that any single reconstructed waveform may not be sufficient to compute time of flight. If the waveform were consistent enough, it may be adequate to just use the first crossing as the time of flight. However, in many embodiments, the computed waveform may need to be evaluated against a known template to determine the best match/alignment.

FIG. 2B shows the performance of the techniques described herein using complete, raw ultrasound waveform sampled at 100 MHz. As shown, the calculated units of fluid dispensed from the drug cartridge are well aligned with the actual units dispensed, and are well within the acceptable tolerance for error (i.e., required performance envelope).

Figure 3:
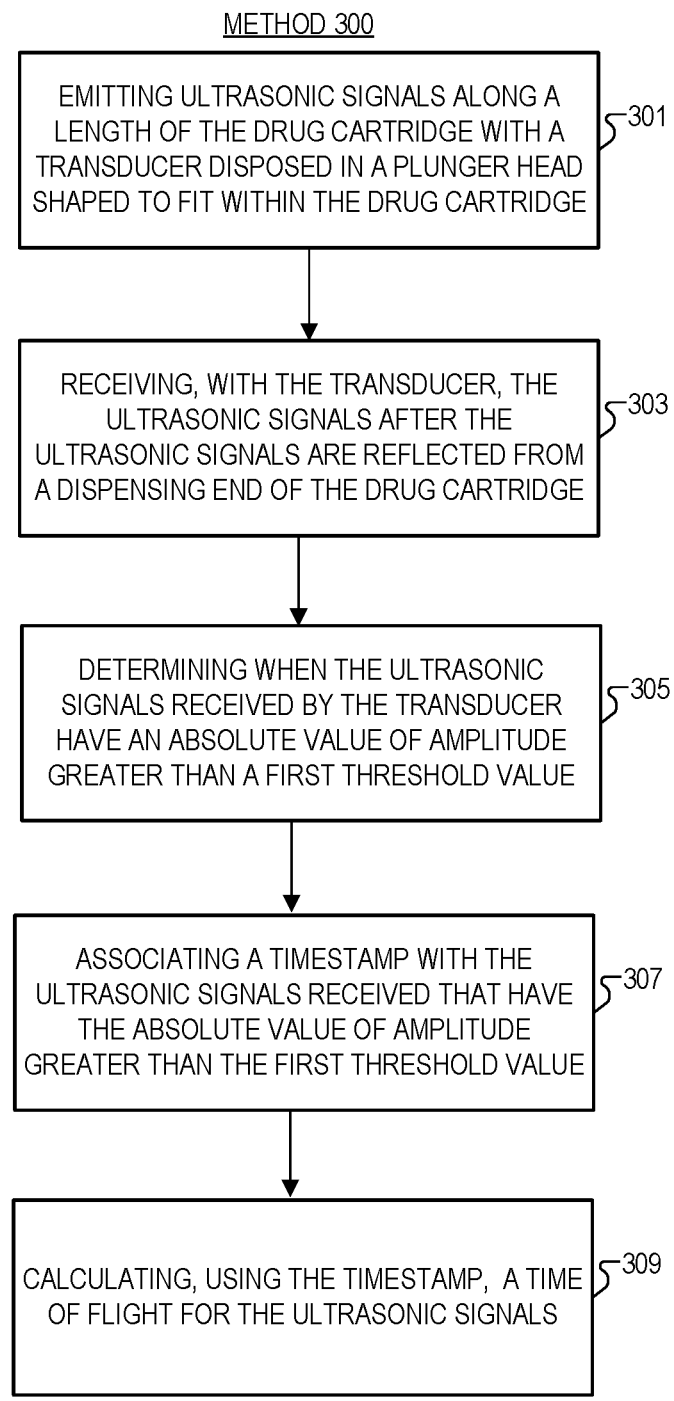
FIG. 3 is a flow chart illustrating a method of monitoring a quantity of fluid in a drug cartridge, in accordance with several embodiments of the disclosure.

FIG. 3 is a flow chart illustrating a method 300 of monitoring a quantity of fluid in a drug cartridge, in accordance with several embodiments of the disclosure. The order in which some or all of process blocks 301-309 appear in method 300 should not be deemed limiting. Rather, one of ordinary skill in the art having the benefit of the present disclosure will understand that some of method 300 may be executed in a variety of orders, not illustrated, or even in parallel. Further, blocks may be added or removed from method 300 in accordance with the teaching of the present disclosure.

Block 301 shows emitting ultrasonic signals along a length of the drug cartridge with a transducer disposed in a plunger head shaped to fit within the drug cartridge. In some embodiments, a voltage is applied across a piezoelectric material and then the circuit is shorted to produce vibrations which form the ultrasonic signal.

Block 303 illustrates receiving, with the transducer, the ultrasonic signals after the ultrasonic signals are reflected from a dispensing end of the drug cartridge. In some embodiments, the transducer may deform when hit by the reflected ultrasound signals which causes the voltage applied to the transducer to change. Accordingly, the controller may receive these voltage changes.

Block 305 depicts determining when the ultrasonic signals received by the transducer have an absolute value of amplitude greater than a first threshold value. For example, if the threshold is 2.7 V and the ultrasonic signals have an absolute value of amplitude that causes a 2.8 V response in the transducer, the controller will determine that an ultrasonic signal with sufficient amplitude has been received.

Block 307 illustrates associating a timestamp with the ultrasonic signals received that have an absolute value of amplitude greater than a first threshold value (e.g., if the voltage across the transducer reaches a certain absolute value of voltage, the controller will associate a timestamp). It is appreciated that the timestamp may be facilitated using an oscillator, clock, or other timing circuitry. As shown in FIGS. 2A and 2B, associating the timestamp may include associating a plurality of timestamps, including the timestamp. In some embodiments, there may be more than one threshold value that that causes the controller to associate a timestamp.

Block 309 shows calculating, using the timestamp, a time of flight for the ultrasonic signals to travel from the transducer to the dispensing end of the drug cartridge and back to the transducer. Using the time of flight, at least one of a position of the plunger head in the drug cartridge, a volume of the fluid in the drug cartridge, or a volume of the fluid dispensed from the drug cartridge may also be calculated. It is appreciated that these calculations may be performed by the controller or circuitry in the plunger head, or may be performed by a remote device.

The time of flight may be derived by fitting a curve to the plurality of timestamps and, once the curve is fitted, the curve's relative position (or phase offset) is estimated relative to a template. Fitting the curve may include using a spline function or the like. In some embodiments, after applying the spline function, the curve is filtered (e.g., high-pass filter) to yield a group of waves with substantially the same period.

The processes explained above are described in terms of computer software and hardware. The techniques described may constitute machine-executable instructions embodied within a tangible or non-transitory machine (e.g., computer) readable storage medium, that when executed by a machine (e.g., a controller) will cause the machine to perform the operations described. Additionally, the processes may be embodied within hardware, such as an application specific integrated circuit ("ASIC") or otherwise. A controller may include a processing apparatus (e.g., a general purpose processor, specific processor like an ASIC, or the like), and memory which may include firmware or software.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method of calculating a quantity of fluid dispensed from a drug cartridge, comprising:
   emitting ultrasonic signals along a length of the drug cartridge with a transducer;
   receiving, with the transducer, the ultrasonic signals after the ultrasonic signals are reflected;
   determining when an absolute value of amplitude of the ultrasonic signals received by the transducer crosses a first threshold value;
   associating timestamps with the ultrasonic signals received for instances that the absolute value of amplitude crosses the first threshold value;
   generating a reconstructed waveform by fitting a curve to the timestamps;
   comparing the reconstructed waveform to an expected waveform recorded at a known position of a plunger head in the drug cartridge; and
   determining a position of the plunger head within the drug cartridge based upon the comparing.

2. The method of claim 1, further comprising determining a time of flight for the ultrasonic signals to travel from the transducer to a dispensing end of the drug cartridge and back to the transducer based upon the reconstructed waveform.

3. The method of claim 2, further comprising calculating at least one of a position of the plunger head in the drug cartridge, a volume of the fluid in the drug cartridge, or a volume of the fluid dispensed from the drug cartridge based upon multiple different reconstructed waveforms, including the reconstructed waveform.

4. The method of claim 1, wherein fitting the curve includes using a spline function.

5. The method of claim 1, further comprising:
   high pass filtering the curve to yield a series of oscillations with substantially a same period to reject higher amplitude, lower frequency curve fits.

6. The method of claim 1, wherein associating the timestamps includes associating the timestamps when the ultrasonic signals received have the absolute value of amplitude greater than the first threshold value or a second threshold value which is different than the first threshold value.

7. The method of claim 1, wherein determining when the absolute value of amplitude of the ultrasonic signals received by the transducer crosses the first threshold value includes determining when either a rising edge or a falling edge of the ultrasonic signals received is greater than the first threshold value.

8. The method of claim 1, wherein determining when the absolute value of amplitude of the ultrasonic signals received by the transducer crosses the first threshold comprises:
   determining when the ultrasonic signals received by the transducer cross a voltage threshold with digital logic circuitry of a microcontroller disposed within the plunger head, wherein a digital input pin of the microcontroller is coupled to receive an analog signal from the transducer.

9. The method of claim 1, wherein the transducer is disposed in the plunger head, which is shaped to fit within the drug cartridge, and wherein the ultrasonic signals are reflected from a dispensing end of the drug cartridge.

* * * * *